United States Patent [19]

Boré et al.

[11] 4,208,402

[45] Jun. 17, 1980

[54] PROCESS FOR IMPROVING THE APPEARANCE OF OILY HAIR OR SKIN

[75] Inventors: Pierre Boré, Montfermeil; Lucienne Tourenq, Livry Gargan, both of France

[73] Assignee: L'Oreal, Paris, France

[21] Appl. No.: 758,329

[22] Filed: Jan. 10, 1977

[51] Int. Cl.$^2$ .......................... A61K 7/00; A61K 7/06; A61K 7/48

[52] U.S. Cl. ................................... 424/70; 424/65; 424/69; 424/78; 424/80; 424/360; 424/DIG. 1; 424/DIG. 2

[58] Field of Search ............... 424/63, 65, 70, 78, 424/80, 359, 360, 361, 362, 363, DIG. 1, DIG. 2

[56] References Cited

U.S. PATENT DOCUMENTS 2,704,269  3/1955  Tice ........................................ 424/360

FOREIGN PATENT DOCUMENTS 2010776 10/1970 Fed. Rep. of Germany ........... 424/360
1484652  5/1967 France ..................................... 424/63

OTHER PUBLICATIONS

Goodman, Cos Derm. McGraw-Hill, NY; 1936, pp. 513, 514, 517.
Janistyn, Handbuch der Kos. and Riechstoffe Huthigverlag, Heidelberg, Ban I, p. 433.
Popescu, Chem. Abs. vol. 53, 1959, p. 6530g.

*Primary Examiner*—Anna P. Fagelson
*Attorney, Agent, or Firm*—Cushman, Darby & Cushman

[57] ABSTRACT

A process for improving the appearance of oily hair or skin, including the scalp, comprises applying thereto an effective amount of an aqueous or hydroalcoholic solution of gelatin present in an amount of about 0.5 to 1.5 percent by weight thereof.

12 Claims, No Drawings

PROCESS FOR IMPROVING THE APPEARANCE OF OILY HAIR OR SKIN

The present invention relates to a cosmetic process for improving the appearance of oily hair or skin.

It is known that the lipid film present on the surface of the scalp is essentially sebum secreted by the sebaceous glands and that the skin lipids originate from the epidermis cell. It is generally accepted that the generic term "sebum" includes both these oily phases.

Starting at puberty, and generally for a period of about 10-20 years, an exaggerated functioning of the sebaceous glands has been found to occur, thus producing an increase of a lipid film on the skin or scalp and hair which thus take on a glossy and oily appearance. Under these circumstances, the hair appears heavy and sticky and is difficult to style. Correlatively, the time within which this oily condition reappears diminishes and to maintain a suitable cosmetic appearance of the hair for styling, the hair must be frequently shampooed.

Numerous studies have been devoted for a long time to this problem and two entirely different solutions appear feasible.

A first solution consists of a biological or medical treatment which is addressed to complex intimate phenomena and which comprises most often an oral administration of certain substances to regulate, particularly, hormonal equilibrium. This solution involves then the use of anti-seborrheic products which retard the functioning of the sebaceous glands.

A second solution comprises a cosmetic treatment which, in contrast to the first solution, does not involve products which retard sebum secretion. Rather, the treatment involves a modification of the appearance of the hair or skin by masking the lipid film, in other words, a diminution of the unfortunate cosmetic effects caused by the presence of excess lipids on the human hair or skin.

Presently, sebum absorbing products are employed to provide an extensive variety of dry shampoo formulations. However, these shampoo formulations are based on such sebum absorbing powders as talc, kaolin, starch or various synthetic polymers. However, the use of these sebum absorbing materials impart a whitish powdery appearance to the hair which is quite difficult to eliminate simply by brushing due to the electrical charges created by the repeated brushing of the keratinic fibers. These electrical charges inhibit a complete removal of such powdered materials.

It has now been found that the use of an aqueous solution of gelatin significantly improves the appearance of oily hair or skin by modifying and/or masking this oily condition.

Thus one embodiment of the present invention relates to a process comprising applying to the skin or scalp or to the hair, an aqueous solution containing from 0.5 to 1.5 percent by weight gelatin, and thereafter drying the hair or permitting it to dry.

The more the skin and/or the hair exhibits an oily appearance, the greater is the quantity of gelatin applied thereto by the application of increased amounts of said aqueous solution.

Preferably, the concentration of the gelatin in the aqueous solution varies between 0.6 and 1.2, particularly between 0.8 and 1.2 weight percent.

The aqueous gelatin solution which is also preferably a hydroalcoholic solution thereof can contain for example from 0 to 30 weight percent of a cosmetically acceptable alcohol, such as ethanol or isopropanol. Generally, the gelatin also contains a preservative which is an anti-bacteria agent and/or an antioxidant. The lotion thus provided can be colored and/or perfumed if desired. In the lotion of the present invention, the gelatin is essentially the only active or principal component thereof. Such a lotion is designated herein as a lotion containing gelatin as the main ingredient. That is to say that, (except for the presence of the solvents, coloring agents, perfumes and preservatives) the gelatin is the only active component (active component here means a component which is active against the oily appearance of hair or skin).

Where the lotion is destined to be applied to the hair, the aqueous or hydroalcoholic solution of gelatin can also contain, in an amount lower than 30 percent relative to the weight of the gelatin present in the solution, a cosmetic film forming polymer which is soluble in water or in a hydroalcoholic solution and which gives after evaporation of the solvent, a transparent film which improves the appearance and the feel of the hair. This polymer is preferably one which is capable of giving alone, in a 4% solution thereof (e.g. aqueous solution) at 25° C., a viscosity lower than 5 cps.

Obviously, these polymers must certainly be compatible with gelatin and must contribute to the improvement of the appearance and feel of the hair.

A lotion containing such polymers, in addition to the gelatin as the only active component, is considered herein to be a composition "containing gelatin as the main ingredient" as defined above.

Representative polymers include, for instance, those partially hydrolyzed polyvinyl acetates, which in a 4% aqueous solution thereof having a viscosity lower than 5 cps at 25° C. Such partially hydrolyzed polyvinyl acetates include those whose ester index is lower than 200, and particularly lower than 150. They are available commercially, for instance, under the names of "Rhodoviol 4/20" and "Rhodoviol 4/125".

The process of the invention is preferably carried out according to the following modes of execution.

In accordance with one mode of execution, a process of the present invention for improving the appearance of oily hair comprises applying to the hair a gelatin solution such as defined above, in an amount sufficient to impregnate the hair, combing the hair and then drying the hair.

This first mode of executing the process of the invention is preferably carried out approximately at the mid-period between two consecutive hair shampooings. For instance, if the hair is shampooed every four or eight days, then the process of this invention will be carried out on the hair thus washed, two or four days, respectively, after the shampooing.

The gelatin solution is applied in an amount sufficient to impregnate the hair although it is desirable to avoid using an excess amount thereof. Generally from 5 to 20 cc of the said gelatin solution are applied to the hair.

Preferably, this first mode of executing the process of this invention comprises impregnating the hair with the gelatin solution, accompanied by, if desired, lightly massaging the hair, untangling the hair by combing, and if desired, leaving the gelatin solution as such in contact with the hair for a few minutes, for example about 2–10 minutes, then drying the hair, and thereafter combing and/or brushing the hair.

The present invention also relates to a second mode of executing the process of this invention to improve the appearance of oily hair which comprises applying to the scalp, with an appropriate applicator, a gelatin solution such as defined above and then drying the hair.

In accordance with this second mode of execution, the gelatin solution is applied to the scalp in an amount sufficient to impregnate it. This impregnation can be effected in accordance with known techniques for impregnating the scalp and/or the base of the hair which include preferably rubbing the scalp with for example a cotton pad impregnated with the gelatin solution, or again with the use of a small dimensioned applicator insertable within the mouth of the container for the gelatin solution.

According to this second mode of execution, the process of the present invention is carried out shortly after a shampooing, generally 24 hours thereafter.

The application of the gelatin solution according to this second mode of execution can, if desired, be repeated 48 hours after the shampooing or even daily. In this latter case, it is advantageous to utilize solutions having a weak gelatin content, or to use only a small amount of the gelatin solution.

To effectuate the process of the present invention according to said first or second modes of execution, the aqueous gelatin solution can contain from 0 to 30 percent and, particularly, from 5 to 25 percent by weight of an alcohol as described above.

The present invention also relates to a third mode of execution, which comprises applying to the skin, and particularly the face, having an oily and shiny appearance, and wherever thereon it is considered necessary, a gelatin solution such as defined above and the leaving the thus treated skin to dry.

This third mode of execution of the process of the present invention can be carried out principally in the following manner: the skin is impregnated with the gelatin solution using a cotton wad and the solution is patted or rubbed thereon, particularly those areas having an oily appearance. Then the skin is left to dry. This application of the gelatin solution is preferably carried out after having first washed the skin.

To effectuate the process of the invention, according to this third mode of execution, preferably a gelatin solution containing not more than 15 weight percent alcohol such as ethanol or isopropanol is employed.

The invention also relates to a cosmetic composition for masking the oily appearance of the hair and/or the skin, said composition consisting essentially of a gelatin solution such as defined above.

Thus the present invention relates principally to processes and/or compositions described in the following nonlimiting examples. Unless otherwise specified, all parts and percentages are by weight.

EXAMPLES OF COMPOSITIONS AND APPLICATION

EXAMPLE 1

In accordance with the present invention, a lotion to improve and mask the appearance of oily hair is prepared by admixing the following components:

| | |
|---|---|
| Ethyl alcohol | 30 g |
| Methyl para-hydroxybenzoate | 0.2 g |
| Gelatin | 1.5 g |
| Perfume | 0.02 g |
| Anti-oxidant | 0.06 g |
| Sterile, demineralized water, q.s.p. | 100 g |

On the third day following a conventional hair shampooing operation, 10 to 20 cc of the above lotion are applied to the hair which has by that time an oily appearance. The hair is then combed and dried. The hair thus treated exhibits a pleasant appearance and feel and is comparable in appearance to hair having just been shampooed.

EXAMPLE 2

In accordance with the present invention, a lotion to improve the appearance of oily hair is prepared by admixing the following components:

| | |
|---|---|
| Isopropyl alcohol | 25 g |
| 1(3-chloroallyl)-3,5,7-triaza-1 azania adamantane (preservative) | 0.1 g |
| Gelatin | 1 g |
| Perfume | 0.1 g |
| Anti-oxidant | 0.05 g |
| Polyvinyl acetate partially hydrolyzed, having a viscosity of 4 cps in a 4% aqueous solution at ≃° C. and known under the trade name "Rhodoviol 4/20" | 0.25 g |
| Sterile, demineralized water, q.s.p. | 100 g |

As a result of the application of 5–10 cc of this lotion, four days after a conventional shampooing, the hair which, prior to this application, exhibited an unaesthetic and oily appearance, exhibited subsequent to said application and after combing and drying the same, a normal non-oily appearance. Further, the hair had good holding power and was pleasant to the touch.

EXAMPLE 3

In accordance with the present invention, a composition for application to the scalp and/or the base of the hair, is prepared by admixing the following components:

| | |
|---|---|
| Ethyl alcohol | 15 g |
| Propyl para hydroxy benzoate | 0.2 g |
| Gelatin | 0.8 g |
| Perfume | 0.05 g |
| Sterile, demineralized water, q.s.p. | 100 g |

This lotion composition is slowly applied to the scalp and/or at the base of the hair with the aid of an applicator. The hair is then untangled and dried. The oily appearance of the scalp is eliminated and the re-appearance of this oily condition is significantly delayed.

Preferably, such a lotion is applied 24 hours after a shampoo, which eliminates too frequent washing of the hair. This application treatment can again be repeated 48 hours after shampooing the hair.

EXAMPLE 4

In accordance with the present invention, a lotion to mask the oily appearance of the skin, and principally the face, is prepared by admixing the following components:

| | |
|---|---|
| Ethyl alcohol | 10 g |
| 2-bromo-2-nitropropane-1,3 diol (preservative) | 0.2 g |
| Gelatin | 1 g |
| Perfume | 0.03 g |
| Anti-oxidant | 0.06 g |
| Sterile, demineralized water, q.s.p. | 100 g |

After application of this lotion, using a cotton wad on those parts of the face having an oily and shiny appearance (chin, nose, etc.), the skin exhibits a normal appearance, i.e. it is no longer shiny.

EXAMPLE 5

In accordance with the present invention, a lotion for application to oily skin is prepared by admixing the following components:

| | |
|---|---|
| Ethyl alcohol | 8 g |
| Methyl para hydroxy benzoate | 0.2 g |
| Gelatin | 1.2 g |
| Perfume | 0.01 g |
| Anti-oxidant | 0.05 g |
| Sterile, demineralized water, q.s.p. | 100 g |

This lotion, when applied to the oily parts of the face with the aid of a pad, imparts to the face a normal, non-shiny appearance.

EXAMPLE 6

A lotion for application to oily appearing hair is prepared by admixing the following components:

| | |
|---|---|
| Ethanol | 15 g |
| Methyl and propyl para hydroxy benzoate | 0.2 g |
| Gelatin | 1 g |
| Rhodoviol 4/125 | 0.2 g |
| Perfume | 0.05 g |
| Sterile, demineralized water, q.s.p. | 100 g |

This lotion can be used as described above in Examples 1-3. By this treatment, the oily appearance is eliminated and the re-appearance of this oily condition of the hair between two consecutive shampooings is significantly delayed.

EXAMPLE 7

A lotion for application to skin having an oily appearance is prepared by admixing the following components:

| | |
|---|---|
| Ethanol | 15 g |
| Methyl and propyl para hydroxy benzoate | 0.2 g |
| Gelatin | 1 g |
| Perfume | 0.02 g |
| Anti-oxidant | 0.06 g |
| Sterile, demineralized water | 100 g |

As a result of the application of this lotion to the face, the shiny and oily appearance thereof is essentially eliminated.

EXAMPLE 8

A lotion for application to hair having an oily appearance was prepared by admixing the following components:

| | |
|---|---|
| Ethanol | 40 g |
| Gelatin | 0.6 g |
| Rhodoviol 4/125 | 0.15 g |
| Perfume | 0.05 g |
| Water, q.s.p. | 100 g |

This lotion can be used as described above in Examples 1-3. The oily appearance, and the re-appearance of this oily condition between two consecutive shampooings is eliminated.

EXAMPLE 9

A lotion for application to oily skin was prepared by admixing the following components:

| | |
|---|---|
| Ethanol | 15 g |
| Gelatin | 0.6 g |
| Rhodoviol 4/20 | 0.06 g |
| Perfume | 0.04 g |
| Sterile, demineralized water q.s.p. | 100 g |

This lotion, when applied to the oily parts of the face, eliminates the shiny and oily appearance.

What is claimed is:

1. A process for improving the appearance of hair, facial skin, or both, of a person whose sebaceous glands secrete excessive amounts of sebum which causes an oily appearance of said hair, said facial skin or both comprising
applying thereto, in an amount effective to improve said appearance by diminishing said oily appearance, a composition which is an aqueous or hydroalcoholic solution containing 0.5 to 1.5% by weight gelatin and partially hydrolyzed polyvinyl acetate, in an amount less than 30 weight percent, relative to the weight of gelatin present in said solution, said partially hydrolyzed polyvinyl acetate being soluble in water or in a hydroalcoholic solution wherein said partially hydrolyzed polyvinyl acetate has a viscosity at 25° C. lower than 5 cps in a 4% solution thereof.

2. A process for improving the appearance of hair of a person suffering from excessive secretion of sebum from the sebaceous glands, the said hair having an oily appearance due to said secretion, comprising applying to the hair an aqueous or hydroalcoholic solution of 0.5 to 1.5% by weight gelatin which also contains a cosmetic film forming polymer in an amount less than 30 weight percent relative to the weight of the gelatin present in said solution, said film forming polymer being soluble in water or in a hydroalcoholic solution, and providing, after evaporation of the solvent, a transparent film which improves the appearance and feel of said hair; wherein said film forming polymer has a viscosity at 25° C. lower than 5 cps in a 4% solution thereof.

3. The process of claim 2 wherein said film forming polymer is partially hydrolyzed polyvinyl acetate.

4. The process of claim 3 wherein said partially hydrolyzed polyvinyl acetate has an ester index lower than 200.

5. The process of claim 3 wherein said partially hydrolyzed polyvinyl acetate has an ester index lower than 150.

6. The process of claim 2 wherein said solution is applied to the hair in an amount sufficient to impregnate the hair, then the hair is combed and dried.

7. The process of claim 6 wherein said process is carried out on hair washed 2 to 4 days prior to application of said solution.

8. The process of claim 2 wherein said solution is applied to the scalp in an amount sufficient to impregnate the hair.

9. The process of claim 8 wherein application is effected 24 hours after a shampooing.

10. The process of claim 9, wherein the application is repeated daily.

11. A cosmetic composition for diminishing the oily appearance of hair or facial skin of a person whose sebaceous glands secrete excessive amounts of sebum and thus cause said hair or facial skin to have an oily and shiny appearance consisting essentially of an aqueous or hydroalcoholic solution of gelatin present in an amount ranging from 0.5 to 1.5 weight percent thereof and partially hydrolyzed polyvinyl acetate, in an amount less than 30 percent by weight relative to the weight of gelatin present in said composition, said partially hydrolyzed polyvinyl acetate being soluble in water or in a hydroalcoholic solution and having a viscosity at 25° C. lower than 5 cps in a 4% solution thereof.

12. The composition of claim 11 wherein said partially hydrolyzed polyvinyl acetate has an ester index lower than 200.

* * * * *

UNITED STATES PATENT AND TRADEMARK OFFICE
CERTIFICATE OF CORRECTION

PATENT NO. : 4,208,402
DATED : June 17, 1980
INVENTOR(S) : Pierre Bore and Lucienne Tourenq It is certified that error appears in the above-identified patent and that said Letters Patent are hereby corrected as shown below:

In the Heading

Please add - -

[30] Foreign Application Priority Date

January 14, 1976 [FR] France 76 00835 - -

Signed and Sealed this

Twenty-fifth Day of November 1980

[SEAL]

Attest:

SIDNEY A. DIAMOND

Attesting Officer

Commissioner of Patents and Trademarks